United States Patent
Satek et al.

(10) Patent No.: US 6,680,419 B2
(45) Date of Patent: Jan. 20, 2004

(54) PROCESS ENHANCING ADSORBENT CAPACITY FOR ACETYLENIC COMPOUNDS

(75) Inventors: Larry C. Satek, St. Charles, IL (US); Michael J. Foral, Aurora, IL (US); Diadema N. Ventura, Lisle, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 09/998,076

(22) Filed: Nov. 30, 2001

(65) Prior Publication Data

US 2003/0105377 A1 Jun. 5, 2003

(51) Int. Cl.⁷ .............................. C07C 7/00; C07C 7/12
(52) U.S. Cl. ...................... 585/829; 585/809; 585/820; 585/826
(58) Field of Search ................................ 585/824, 826, 585/809, 820

(56) References Cited

U.S. PATENT DOCUMENTS

| | | | |
|---|---|---|---|
| 2,882,244 A | 4/1959 | Milton | 252/455 |
| 3,130,007 A | 4/1964 | Breck | 23/113 |
| 3,243,470 A * | 3/1966 | Davis et al. | 585/829 |
| 3,702,886 A | 11/1972 | Argauer et al. | 423/328 |
| 3,709,979 A | 1/1973 | Chu | 423/328 |
| 3,755,488 A | 8/1973 | Johnson et al. | 260/677 A |
| 3,792,981 A | 2/1974 | Hettick et al. | 23/288 R |
| 3,812,057 A | 5/1974 | Morgan et al. | 252/416 |
| 3,832,449 A | 8/1974 | Rosinski et al. | 423/328 |
| 3,912,789 A | 10/1975 | Frevel et al. | 260/681.5 |
| 4,019,879 A | 4/1977 | Rabo et al. | 55/68 |
| 4,034,065 A | 7/1977 | Kasai et al. | 423/328 |
| 4,268,420 A | 5/1981 | Klotz | 252/432 |
| 4,269,813 A | 5/1981 | Klotz | 423/277 |
| 4,292,457 A | 9/1981 | Klotz | 585/447 |
| 4,292,458 A | 9/1981 | Klotz | 585/469 |
| 4,425,255 A | 1/1984 | Toyoda et al. | 502/38 |
| 4,717,398 A | 1/1988 | Pearce | 55/58 |
| 4,926,001 A | 5/1990 | Alagy et al. | 585/500 |
| 5,332,705 A | 7/1994 | Huang et al. | 502/53 |
| 6,080,905 A | 6/2000 | Kaminsky et al. | 585/829 |
| 6,124,517 A | 9/2000 | Kaminsky et al. | 585/829 |
| 6,215,037 B1 | 4/2001 | Padin et al. | 585/809 |

* cited by examiner

Primary Examiner—Walter D. Griffin
Assistant Examiner—Tam M. Nguyen
(74) Attorney, Agent, or Firm—James R. Henes (57) ABSTRACT

Processes using heterogeneous adsorbents are disclosed for purification of olefins such as are typically produced by thermal cracking of suitable hydrocarbon feedstocks, by providing a impure mixture comprising at least one olefin of from 2 to about 8 carbon atoms, acetylenic impurities having the same or similar carbon content in an amount of up to about 1 percent by volume base upon the total amount of olefin present and optionally saturated hydrocarbon gases; admixing a source of dihydrogen with the impure mixture to form a feedstream comprising a sub-stoichiometric amount of dihydrogen based upon conversion of the total amount of acetylenic impurities present to their olefinic analogs; and passing the feedstream through a particulate bed of adsorbent comprising predominantly a support material on which is dispersed at least one metallic element in the zero valent state, to effect, under conditions suitable for adsorption within the bed, selective adsorption and/or complexing of the contained acetylenic contaminants with the adsorbent, and thereby obtain purified olefinic product which contains less than about 1 part per million by volume of the acetylenic impurities. Thereafter the resulting bed of adsorbent is regenerated in the presence of a reducing gas containing dihydrogen to effect release of the contained acetylenic impurities from the adsorbent.

17 Claims, 2 Drawing Sheets

PROCESS ENHANCING ADSORBENT CAPACITY FOR ACETYLENIC COMPOUNDS

FIELD OF THE INVENTION

The field of this invention relates to use of heterogeneous adsorbents in purification of relatively impure olefins such as are typically produced by thermal cracking of suitable hydrocarbon feedstocks. More particularly, this invention concerns purification by passing an olefinic process stream, containing small amounts of acetylenic impurities, and optionally carbon oxides and/or other organic components which are, typically, impurities in cracked gas, through a particulate bed of heterogeneous adsorbent comprising a metal supported on a high surface area carrier, under conditions suitable for adsorption of alkynes. Beneficially, a limited amount of dihydrogen is fed into the bed during treatment of the olefinic process stream thereby increasing capacity of the adsorbent for acetylenics.

Beneficially, a sub-stoichiometric amount of dihydrogen is admixed with the olefinic process stream fed into the bed thereby increasing capacity of the adsorbent for acetylenics.

Processes according to this invention are particularly useful where the olefin being purified is ethylene and/or propylene formed by thermal cracking of hydrocarbon feedstocks.

BACKGROUND OF THE INVENTION

As is well known, olefins, or alkenes, are a homologous series of hydrocarbon compounds characterized by having a double bond of four shared electrons between two carbon atoms. The simplest member of the series, ethylene, is the largest volume organic chemical produced today. Olefins including, importantly, ethylene, propylene and smaller amounts of butadiene, are converted to a multitude of intermediate and end products on a large scale, mainly polymeric materials.

Commercial production of olefins is, almost exclusively, accomplished by pyrolysis of hydrocarbons in tubular reactor coils installed in externally fired heaters. Thermal cracking feed stocks include streams of ethane, propane or a hydrocarbon liquid ranging in boiling point from light straight-run gasoline through gas oil. Because of the very high temperatures employed, commercial olefin processes invariably coproduce significant amounts of acetylene and methyl acetylene. Required separation of the acetylene from the primary olefin can, considerably, increase the plant cost.

In a typical ethylene plant the cracking section represents about 25 percent of the cost of the unit while the compression, heating, dehydration, recovery and refrigeration sections represent the remaining about 75 percent of the total. This endothermic process is carried out in large pyrolysis furnaces with the expenditure of large quantities of heat which is provided in part by burning the methane produced in the cracking process. After cracking, the reactor effluent is put through a series of separation steps involving cryogenic separation of products such as ethylene and propylene. The total energy requirements for the process are thus very large and ways to reduce it are of substantial commercial interest. In addition, it is of interest to reduce the amount of methane and heavy fuel oils produced in the cracking processor to utilize it other than for its fuel value.

Hydrocarbon cracking is carried out using a feed which is ethane, propane or a hydrocarbon liquid ranging in boiling point from light straight-run gasoline through gas oil. Ethane, propane, liquid naphthas, or mixtures thereof are preferred feed to a hydrocarbon cracking unit. Hydrocarbon cracking is, generally, carried out thermally in the presence of dilution steam in large cracking furnaces which are heated by burning, at least in part, methane and other waste gases from the olefins process resulting in large amounts of NOx pollutants. The hydrocarbon cracking process is very endothermic and requires large quantities of heat per pound of product. However, newer methods of processing hydrocarbons utilizes at least to some extent catalytic processes which are better able to be tuned to produce a particular product slate. The amount of steam used per pound of feed in the thermal process depends to some extent on the feed used and the product slate desired. Typically, steam pressures are in the range of about 30 lbs per sq in to about 80 lbs per sq in, and amounts of steam used are in the range of about 0.2 pounds of steam per pound of feed to 0.7 pounds of per pound of feed. The temperature, pressure and space velocity ranges used in thermal hydrocarbon cracking processes to some extent depend upon the feed used and the product slate desired which are well known as may be appreciated by one skilled in the art.

The type of furnace used in the thermal cracking process is also well known. However the ceramic honeycomb furnace which is described in U.S. Pat. No. 4,926,001, the contents of which patent are specifically incorporated herein by reference, is an example of a new type of cracking which could have a special utility for this process.

Several methods are known for separation of an organic gas containing unsaturated linkages from gaseous mixtures. These include, for instance, cryogenic distillation, liquid adsorption, membrane separation and the so called "pressure swing adsorption" in which adsorption occurs at a higher pressure than the pressure at which the adsorbent is regenerated. Cryogenic distillation and liquid adsorption are common techniques for separation of carbon monoxide and alkenes from gaseous mixtures containing molecules of similar size, e.g., nitrogen or methane. However, both techniques have disadvantages such as high capital cost and high operating expenses. For example, liquid adsorption techniques suffer from solvent loss and need a complex solvent make-up and recovery system.

Molecular sieves which selectively adsorb carbon monoxide from gaseous mixtures by chemisorption are also known. U.S. Pat. Nos. 4,019,879 and 4,034,065 refer to use of high silica zeolites, which have relatively high selectivities for carbon monoxide, in the pressure swing adsorption method. However, these zeolites only have moderate capacity for carbon monoxide and more particularly require very low vacuum pressures to recover the adsorbed gases and/or to regenerate the zeolite.

U.S. Pat. No. 4,717,398 describes a pressure swing adsorption process for selective adsorption and subsequent recovery of an organic gas containing unsaturated linkages from gaseous mixtures by passing the mixture over a zeolite ion-exchanged with cuprous ions (Cu I) characterized in that the zeolite has a faujasite type crystalline structure (Y).

U.S. Pat. No. 6,215,037 in the name of Joel Padin, Curtis L. Munson and Ralph T. Yang provides a selection of specific zeolites said to be useful for selective adsorption of dienes from mono-olefins. In particular, the adsorbents are ion-exchanged zeolites of the group consisting of zeolite X, Zeolite Y and zeolite LSX in a form having exchangeable cationic sites. According to the patent, essentially all cationic sites of the ion-exchanged zeolite must contain silver cation or copper cation for the selective separation of diene from mono-olefin which the same number of carbon atoms.

Kokai JP Number 50929-1968 describes a method of purifying vinyl compounds containing up to about 10 percent by weight of acetylene compounds including ethyl acetylene, vinyl acetylene and phenyl acetylene whereby the acetylene compounds are adsorbed in an adsorption agent of 1-valent and/or 0-valent copper and/or silver supported on inert carrier such as δ-alumina, silica or active carbon. However, it is well known that acetylene and these acetylene compounds react with copper and/or silver to from copper acetylide or silver acetylide. Both the acetylide of copper and silver are unstable compounds. Because they are explosive under some conditions their possible formation presents safety problems in operation and in handling adsorbent containing such precipitates.

German Disclosure Document 2059794 describes a liquid adsorption process for purification of paraffinic, olefinic and/or aromatic hydrocarbons with an adsorption agent consisting in essence of a complex of a copper (Cu I)-salt with an alkanolamine such as mono-ethanolamine, mono-isopropanolamine, di-ethanolamine, tri-ethanolamine and arylalkanolmines, and optionally in the presence of a glycol or polyglycol. However, the product stream is contaminated with unacceptable levels of components of the such agents absorbed in the hydrocarbon flow. While such contamination might be removable using an additional bed of silica gel, aluminum oxide or a wide-pored molecular sieve, this would involve additional capital costs, operation expenses and perhaps safety problems.

Processes using heterogeneous adsorbents are known for purification of olefins, such as are typically produced by thermal cracking of suitable hydrocarbon feedstocks, by passing a stream of olefin through a particulate bed of support material on which is dispersed a metallic element. U.S. Pat. Nos. 6,080,905 and 6,124,517 in the name of Mark P. Kaminsky, Shiyou Pei, Richard A. Wilsak, and Robert E. Whittaker describe adsorption which is carried out in an essentially dihydrogen-free atmosphere within the bed. Adsorption of the contained acetylenic impurities is continued until levels of acetylenic impurities in the effluent stream increase to a predetermined level. Thereafter the resulting bed of adsorbent is regenerated using hydrogen to effect release of the contained acetylenic impurities from the adsorbent. However, there remains a need to increase the capacity of adsorbents for acetylenics whereby the useful life of the adsorbent bed between regenerations is increased.

Olefin-paraffin separations represent a class of most important and also most costly separations in the chemical and petrochemical industry. Cryogenic distillation has been used for over 60 years for these separations. They remain to be the most energy-intensive distillations because of the close relative volatilities. For example, ethane-ethylene separation is carried out at about −25° C. and 320 pounds per square inch gauge pressure (psig) in a column containing over 100 trays, and propane-propylene separation is performed by an equally energy-intensive distillation at about −30° C. and 30 psig.

Impurity refers to compounds that are present in the olefin plant feedstocks and products. Well-defined target levels exist for impurities. Common impurities in ethylene and propylene include: acetylene, methyl acetylene, methane, ethane, propane, propadiene, and carbon dioxide. Listed below are the mole weight and atmospheric boiling points for the light products from thermal cracking and some common compounds potentially found in an olefins unit. Included are some compounds which have similar boiling temperatures to cracked products and may be present in feedstocks or produced in trace amounts during thermal cracking.

| Compound | Mole Weight | Normal Boiling Point, ° C. |
| --- | --- | --- |
| Hydrogen | 2.016 | −252.8 |
| Nitrogen | 28.013 | −195.8 |
| Carbon monoxide | 28.010 | −191.5 |
| Oxygen | 31.999 | −183.0 |
| Methane | 16.043 | −161.5 |
| Ethylene | 28.054 | −103.8 |
| Ethane | 30.070 | −88.7 |
| Phosphine | 33.970 | −87.4 |
| Acetylene* | 26.038 | −84.0 |
| Carbon dioxide* | 44.010 | −78.5 |
| Radon | 222.00 | −61.8 |
| Hydrogen sulfide | 34.080 | −60.4 |
| Arsine | 77.910 | −55.0 |
| Carbonyl sulfide | 60.070 | −50.3 |
| Propylene | 42.081 | −47.8 |
| Propane | 44.097 | −42.1 |
| Propadiene (PD) | 40.065 | −34.5 |
| Cyclo-propane | 42.081 | −32.8 |
| Methyl acetylene | 40.065 | −23.2 |
| Water | 18.015 | 100. |

*Sublimation temperature

Recently the trend in the hydrocarbon processing industry is to reduce commercially acceptable levels of impurities in major olefin product streams, i.e., ethylene, propylene, and hydrogen. Need for purity improvements is directly related to increasing use of higher activity catalysts for production of polyethylene and polypropylene, and to a limited extent other olefin derivatives.

It is known that acetylenic impurities can be selectively hydrogenated and thereby removed from such product streams by passing the product stream over an acetylene hydrogenation catalyst in the presence of dihydrogen (molecular hydrogen, $H_2$). However, these hydrogenation processes typically result in the deposition of carbonaceous residues or "green oil" on the catalyst which deactivates the catalyst. Therefore, acetylene hydrogenation processes for treating liquid or liquefiable olefins and diolefins typically include an oxygenation step or a "burn" step to remove the deactivating carbonaceous residues from the catalyst followed by a hydrogen reduction step to reactivate the hydrogenation catalyst. For example, see U.S. Pat. No. 3,755,488 to Johnson et al., U.S. Pat. No. 3,792,981 to Hettick et al., U.S. Pat. No. 3,812,057 to Morgan and U.S. Pat. No. 4,425,255 to Toyoda. However, U.S. Pat. Nos. 3,912,789 and 5,332,705 state that by using selected hydrogenation catalysts containing palladium, at least partial regeneration can be accomplished using a hydrogenation step alone at high temperatures (600° F.–700° F.) and in the absence of an oxygenation step.

Selective hydrogenation of the about 2000 to 4000 parts per million of acetylenic impurities to ethylene is, generally, a crucial operation for purification of olefins produced by thermal steam cracking. Typical of a small class of commercially useful catalysts are materials containing very low levels of an active metal supported on an inert carrier, for example a particulate bed having less than about 0.03 percent (300 ppm) palladium supported on the surface skin of carrier pellets having surface area of less than about 10 $m^2/gm$.

Many commercial olefin plants using steam crackers use, generally, front-end acetylene converters, i.e., the hydrogenation unit is fed $C_3$ and lighter cracked gas which feed has a high enough concentration of hydrogen to easily hydrogenate the acetylenic impurities, however, when run improperly, will also hydrogenate a large fraction of the ethylene and propylene product. Both hydrogenation of acetylene and ethylene are highly exothermic as shown below:

$C_2 H_2 + H_2 \longrightarrow C_2 H_4 \quad H = -41 \text{ kcal/mole}$
$C_2 H_4 + H_2 \longrightarrow C_2 H_6 \quad H = -32.7 \text{ kcal/mole}$ Accelerated catalyst deactivation and thermal runaways caused by loss in catalyst selectivity are common problems which plague acetylene converters. Such problems result in unscheduled shutdowns and increased costs to replace deactivated catalyst.

The problem of over-hydrogenation is aggravated because the rate constant for ethylene hydrogenation to ethane is 100 times faster than for the hydrogenation of acetylene to ethylene. As a means to avoid a $C_2 H_4$ hydrogenation thermal runaway, acetylene, carbon monoxide and diolefins concentrations must, therefore, be high enough to cover most active sites so none are left to adsorb ethylene. For example, acetylene, carbon monoxide, methyl acetylene, and propadiene have bond strengths to palladium which are stronger than the ethylene to palladium bonds. Selection of active metal, size of the metal particles and other physical and chemical factors ultimately affect the "operating temperature window" which is the delta of temperature between acetylene conversion to ethylene (typically in a range from about 100° F. to about 150° F.) and thermal runaway where all molecular hydrogen is converted and a large amount of the ethylene is converted to ethane (about 170° F. to about 225° F.). The wider the window, the safer is operation of the unit.

It is therefore a general object of the present invention to provide an improved process which overcomes the aforesaid problem of prior art methods, for production of olefins from thermal cracking of hydrocarbon feed stocks which olefin can be used for manufacture of polymeric materials using higher activity catalysts.

More particularly, it is an object of the present invention to provide an improved method for purification of ethylene and/or propylene containing small amounts of acetylenic impurities, carbon oxides and/or other organic components that are impurities in olefinic process streams, by passing the impure olefin stream through a particulate bed of heterogeneous adsorbent comprising a metal supported on a high surface area carrier, under conditions suitable for adsorption of alkynes impurities.

It is another object of the present invention to provide an improved aforesaid purification method that employs an adsorbent that, even after a substantial period of aging, exhibits ability to withstand repeated regenerations and yet retain useful adsorption capacity. Other objects and advantages of the invention will become apparent upon reading the following detailed description and appended claims.

SUMMARY OF THE INVENTION

Economical processes are disclosed which obtain purified olefinic product by purification of a relatively impure olefins such as are produced, for example, by thermal cracking of hydrocarbons. Processes of this invention comprise providing a impure mixture comprising at least one olefin of from 2 to about 8 carbon atoms, acetylenic impurities having the same or similar carbon content in an amount of up to about 1 percent by volume base upon the total amount of olefin present and optionally saturated hydrocarbon gases; admixing a source of dihydrogen with the impure mixture to form a feedstream comprising a sub-stoichiometeric amount of dihydrogen based upon conversion of the total amount of acetylenic impurities present to their olefinic analogs; passing the feedstream through a particulate bed of adsorbent comprising predominantly a support material having high surface area on which is dispersed at least one metallic element in the zero valent state selected from the group consisting of chromium, iron, cobalt, nickel, copper, ruthenium, palladium, silver and platinum, to effect, under conditions suitable for adsorption within the bed, selective adsorption and/or complexing of the contained acetylenic contaminants with the adsorbent, and thereby obtain purified olefinic product which contains less than about 1 part per million by volume of the acetylenic impurities; and thereafter regenerating the resulting bed of adsorbent in the presence of a reducing gas comprising dihydrogen (molecular hydrogen) to effect release of the contained acetylenic impurities from the adsorbent.

It has been found that the presence of a small amount of dihydrogen in an olefinic feedstream containing acetylenic impurities unexpectedly increases the capacity of the adsorbent for the acetylenics therein. The amount of dihydrogen present in the feedstream beneficially is less than that amount necessary to stoichiometrically hydrogenate all acetylenic impurities to their corresponding olefin.

Another aspect of special significance is the separation of acetylenic impurities from ethylene or propylene containing small amounts of acetylene, i.e., less than about 5000 parts per million by weight of one or more acetylenic impurities, and provide, advantageously, purified product containing less than about 1 parts per million by weight, and frequently even less than about 0.5 parts per million by weight.

In yet another aspect the invention is a process for purification of olefins produced by thermal cracking of hydrocarbons which comprises: providing a impure mixture comprising at least about 99 percent by volume of an olefin having from 2 to about 4 carbon atoms, and acetylenic impurities having the same or similar carbon content in an amount in a range upward from about 1 to about 1000 parts per million by volume; admixing a source of dihydrogen with the impure mixture to form a feedstream comprising a sub-stoichiometric amount of dihydrogen based upon conversion of the total amount of acetylenic impurities present to their olefinic analogs; passing the feedstream through a particulate bed of adsorbent comprising predominantly a support material selected from the group alumina, silica, active carbon, clay and zeolites having surface area in a range of from about 10 to about 2,000 square meters per gram as measured by the BET gas adsorption method, on which is dispersed at least one metallic element selected from the group consisting of chromium, iron, cobalt, nickel, copper, ruthenium, palladium, silver and platinum, to provide an effluent stream from the bed; effecting, under conditions suitable for adsorption within the bed, selective adsorption and/or complexing of the contained acetylenic contaminants with the adsorbent, until levels of the acetylenic impurities in the effluent stream increase to a predetermined level in a range downward from about 1 parts per million by volume; and thereafter regenerating the resulting bed of adsorbent in the presence of a reducing gas comprising dihydrogen to effect release of the contained acetylenic impurities from the adsorbent.

A preferred class of adsorbents useful in processes according the invention, comprises at least about 90 weight percent of a gamma alumina having surface area in a range of from about 80 to about 500 square meters per gram as measured by the BET gas adsorption method, and contains less than 500 parts per million by weight of a sulfur-containing component, calculated as elemental sulfur. More preferred are the adsorbent which comprises at least about 90 weight percent of a gamma alumina having surface area in a range of from about 150 to about 350 square meters per gram as measured by the BET gas adsorption method, and wherein the metal dispersed on the support material is palladium, and the absorbent has a palladium content in a range of from about 0.01 to about 10 percent based on the total weight of the adsorbent.

For a more complete understanding of the present invention, reference should now be made to the embodiments illustrated in greater detail in the accompanying drawing and described below by way of examples of the invention.

BRIEF DESCRIPTION OF THE DRAWINGS

The appended claims set forth those novel features which characterize the present invention. The present invention itself, as well as advantages thereof, may best be understood, however, by reference to the following brief description of preferred embodiments taken in conjunction with the annexed drawing, in which:

BRIEF DESCRIPTION OF THE INVENTION

Processes of this invention are particularly suitable for use in purification of aliphatically unsaturated organic compounds produced, generally, by thermal cracking of hydrocarbons.

Unsaturated compounds of most interest with regard to purification by the method of the present invention, have two to about eight carbon atoms, preferably two to about four carbon atoms, and more preferably ethylene or propylene. The separation of acetylenic impurities from ethylene or propylene which may be contained in admixtures with other normally impure materials, such as one or more of ethane, methane, propane and oxides of carbon is of particular importance. For example mixtures serving as a source of ethylene containing feed for the process may contain about 1 to about 99 weight percent ethylene, and about 0 to about 50 weight percent ethane.

Generally acetylenic impurities described in this invention are expressed by the formula where R and R* are independently hydrogen or a hydrocarbon group of up to 6 carbon atoms.

It is desirable to have low levels of dihydrogen in the olefinic feedstream to the adsorber for removal of contained acetylenic impurities. The presence of the dihydrogen at sub-stoichiometric levels significantly increases the capacity of an important class of adsorbents for acetylenic impurities. The amount of dihydrogen present in impure mixture in the adsorber advantageously is less than that amount necessary to stoichiometrically hydrogenate all acetylenic impurities to their corresponding olefins:

The magnitude of observed increases in capacity of the adsorbents for the acetylenic impurities in the olefinic mixture of gases with sub-stoichiometric levels of dihydrogen are significantly greater than can be accounted as resulting from simple hydrogenation reactions.

Any mercury-containing, arsenic-containing, and sulfur-containing components, e.g., hydrogen sulfide, present in the impure mixture fed to the particulate bed of adsorbent should suitably be removed therefrom in any known manner in order to avoid the risk of poisoning the dispersed metal. The hydrocarbon mixture used in the process of the present invention is suitably a cracked gas from which the majority of the $C_5$ and higher hydrocarbons have been removed. The impure mixture may thus comprise ethylene, propylene, butenes, methane, ethane, propane and butane.

In preferred embodiments of processes according to the invention, the olefin in the impure mixture being purified is predominantly ethylene or propylene, the impure mixture contains less than about 1 parts per million by volume of mercury-containing, arsenic-containing, and sulfur-containing components, each calculated as the element, and wherein the impure mixture, while passing through the bed, is at temperatures in a range upward from about minus 78° C. to about 100° C., preferably in a range of from about minus 5° C. to about 95° C., more preferably in a range of from about 5° C. to about 65° C., and most preferably in a range of from about 10° C. to about 55° C.

The impure mixture used in the process of the present invention may also comprise water and may optionally be saturated with water.

Broadly, according to the present invention, there is provided a particulate bed of adsorbent comprising predominantly a support material having high surface area on which is dispersed at least one metallic element selected from the group consisting of chromium, iron, cobalt, nickel, copper, ruthenium, palladium, silver and platinum. Suitable adsorbents exhibit, in the presence of an olefinic mixture of gasses within the bed, selective adsorption and/or complexing of the acetylenic impurities with the adsorbent. According to the present invention dispersed metal content is in a range of from about 0.01 to about 40 percent based on the total weight of the adsorbent. Preferably dispersed metal content is in a range of from about 0.01 to about 20 percent based on the total weight of the adsorbent.

The adsorbent can, optionally, further comprise one or more elements selected from the group consisting of lithium, sodium, potassium, zinc, molybdenum, tin, tungsten, and iridium, dispersed on the support material. Preferably the adsorbent further comprises a member selected from the group consisting of lithium, sodium, potassium, zinc, molybdenum, and tin dispersed on the support material.

For processes according to invention the metal dispersed on the support material is, advantageously, at least one element selected from the group consisting of chromium, iron, cobalt, nickel, copper, ruthenium, palladium, silver and platinum, and the absorbent has a dispersed metal content in a range of from about 0.05 to about 20 percent based on the total weight of the adsorbent.

More preferred for processes according to this invention are adsorbents having palladium metal dispersed on the support, and the absorbent has a palladium content in a range of from about 0.05 to about 10 percent, more preferred palladium content in a range of from about 0.1 to about 5.0 percent based on the total weight of the adsorbent.

High metal dispersion and loading resulted in higher metal surface area. Capacity of an adsorbent is, typically, related directly to metal surface area. Any method which increases and/or maintains high metal surface area is, therefore, beneficial to achieving high acetylene adsorption capacity.

Preferred for processes according to this invention are adsorbents having a dispersion value of at least about 10 percent, preferably in a range upward from about 20 percent to about 100 percent. Dispersion is a measure of the accessibility of the active metals on the adsorbent. Such dispersion methods are discussed in H. C. Gruber's, *Analytical Chemistry*, Vol. 13, p. 1828, (1962). The adsorbents for use in this invention were analyzed for dispersion using a pulsed carbon monoxide technique as described in more detail in the Examples. Palladium containing adsorbents having large dispersion values are desired because more of the palladium metal is available for adsorption.

Support materials are, advantageously, selected from the group consisting of alumina, silica, carbon, clay and zeolites (molecular sieves). Surface areas of support materials are, preferably, in a range of from about 10 to about 2,000 square meters per gram as measured by the BET gas adsorption method.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Zeolitic materials, both natural and synthetic, useful herein have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

In the past various molecular sieve compositions natural and synthetic have been found to be useful for a number of hydrocarbon conversion reactions. Among these are alkylation, aromatization, dehydrogenation and isomerization. Among the sieves which have been used are Type A, X, Y and those of the MFI crystal structure, as shown in "Atlas of Zeolite Structure Types," Second Revised Edition 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

Manufacture of the ZSM materials utilizes a mixed base system in which sodium aluminate and a silicon containing material are mixed together with sodium hydroxide and an organic base, such as tetrapropylammonium hydroxide and tetrapropylammonium bromide, under specified reaction conditions, to form the crystalline aluminosilicate, preferably a crystalline metallosilicate exhibiting the MFI crystal structure.

A preferred class of molecular sieves useful, according to the present invention, are crystalline borosilicate molecular sieves disclosed in commonly assigned U.S. Pat. Nos. 4,268,420, 4,269,813, 4,292,457, and 4,292,458 to Marvin R. Klotz, which are incorporated herein by reference.

BRIEF DESCRIPTION OF PREFERRED EMBODIMENTS OF THE INVENTION

While this invention is susceptible of embodiment in many different forms, this specification and accompanying drawing disclose only some specific forms as an example of the use of the invention. In particular, preferred embodiments of the invention for purification of a impure mixture comprising olefin preferably an olefin of from two to about eight carbon atoms having a single double bond, acetylenic impurities having the same or similar carbon content and optionally alkanes (paraffin hydrocarbons) and/or alkenes having more than one double bond (di- or tri-olefin hydrocarbons) produced by thermal cracking of hydrocarbons are illustrated and described. The invention is not intended to be limited to the embodiments so described, and the scope of the invention will be pointed out in the appended claims.

Figure 1:
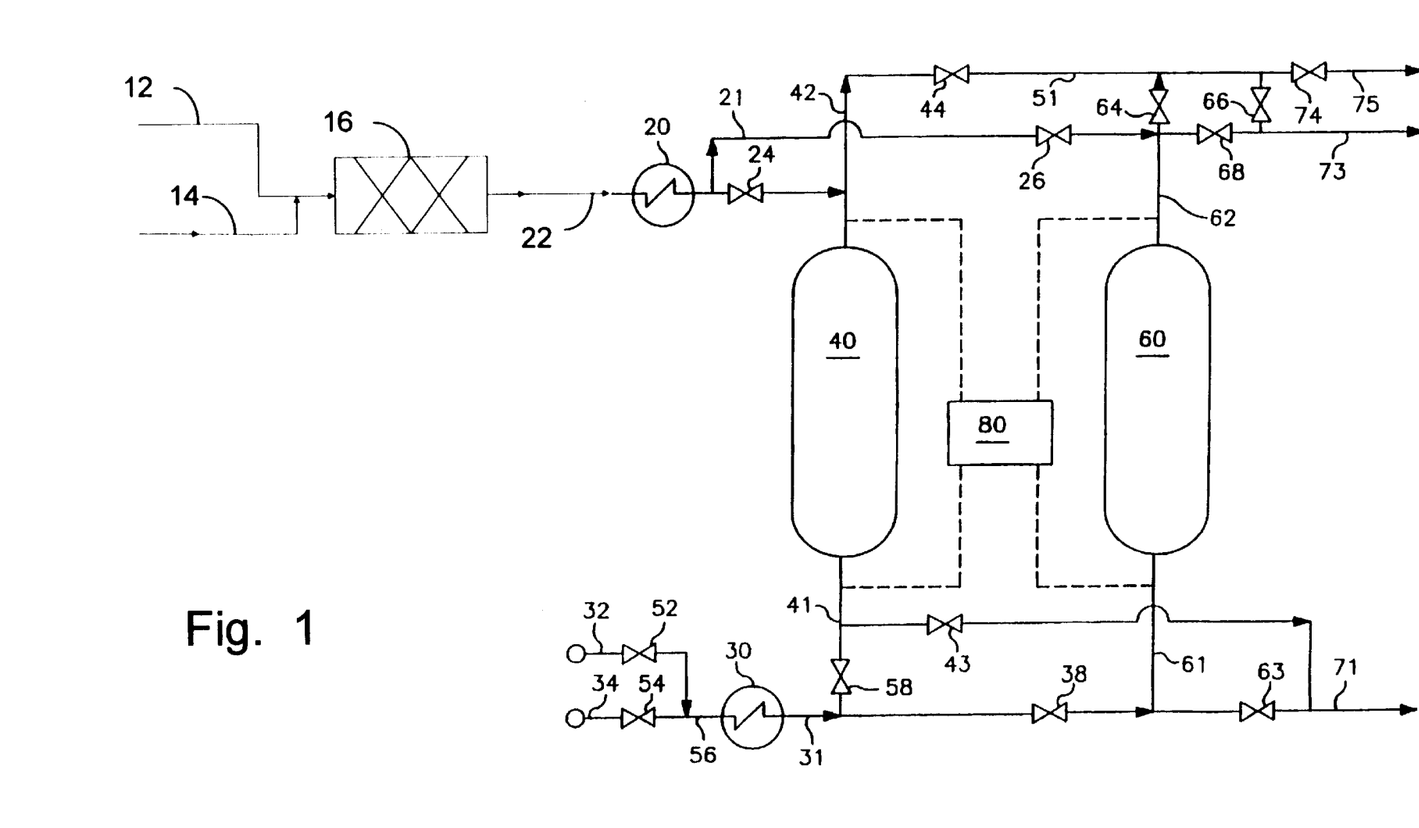
FIG. 1 is a schematic diagram of a preferred method for operating the process of this invention in the continuous mode being arranged to provide sufficient reactants for the reactions and to maintain suitable reaction temperatures in accordance with the present invention.

The apparatus of this invention is used with certain conventional components the details of which, although not fully illustrated or described, will be apparent to those having skill in the art and an understanding of the necessary function of such components. More specifically with reference to the FIGURE, which illustrates an integrated olefin purification system including: an optional feedstream mixer, illustrated mixer 16, one or more optional heat exchangers for controlling temperature of the feedstream to temperatures in a range from about minus 5° C. to about 95° C. (preferably from about 5° C. to about 65° C.) illustrated as feed exchanger 20; adsorption vessels containing one or more particulate beds of a suitable solid adsorbent, illustrated as vessels 40 and 60; and means for analysis of feed and effluent streams, illustrated as on-line analytical system 80.

During operation of the integrated olefin purification system, a impure mixture containing less than about 500 parts per million by weight of the acetylene and optionally carbon monoxide impurities formed by chemical conversions in commercial thermal cracking processes, is, for example ethylene fed from the overhead of a C2 distillation tower or intermediate storage (not shown) through conduit 12 and into feedstream mixer 16. A gaseous source of dihydrogen is fed into feedstream mixer 16. from storage (not shown) through conduit 14. The resulting feedstream which comprises a sub-stoichiometric amount of dihydrogen based upon the total amount of acetylenic impurities present is passed through conduit 22 and into feed exchanger 20 to control temperature during adsorption. Effluent from feed exchanger 20 flows through, manifold 21 and, alternately, through valve 24 and manifold 42 or valve 26 and manifold 62 into one of two adsorption vessels 40 and 60 which contain beds of a suitable solid adsorbent, such as gamma alumina with 1.0 percent palladium based upon the weight of adsorbent.

During operation the gaseous mixture passes though the bed of particulate adsorbent at gas hourly space velocities in a range of from about 0.05 hours$^{-1}$ to about 40,000 hours$^{-1}$ and even higher, preferably from about 0.5 hours$^{-1}$ to about 20,000 hours$^{-1}$ and more preferably from about 0.5 hours$^{-1}$ to about 10,000 hours$^{-1}$.

Compositions of the gaseous feed and effluent of each adsorption vessel is monitored by on-line analytical system 80. While levels of acetylenic impurities in the effluent of the adsorption vessel in purification service are in a range downward from a predetermined level, purified olefin from adsorption vessel 40 and/or adsorption vessel 60 flows through manifold 41, and valve 43 and/or manifold 61 and valve 63, and through manifold 71 directly to pipeline for transportation of polymer grade ethylene, or to storage (not shown). When the level of acetylenic impurities in the effluent of an adsorption vessel in purification service reaches or exceeds the predetermined level, the adsorption vessel is isolated from the process flow by means of valve 24 and valve 43, or valve 26 and 63, and thereafter the resulting bed of loaded adsorbent is treated to effect release of the contained acetylenic impurities from the adsorbent by hydrogenation.

Suitable absorbents have capacity to treat from about 300 to about 40,000 pounds of olefin feed per pound of adsorbent where the olefin feed contains about 0.5 parts per million (ppm) acetylene. Approximately $5\times10^{-4}$ pounds of acetylene to about $1\times10^{-2}$ pounds are, advantageously, adsorbed per pound of adsorbent before regeneration is required.

During continuous operation of this embodiment, the time required for treating, alternately, of the loaded adsorbent to effect release of the contained acetylenic impurities from the adsorbent by hydrogenation, is provided by using two (as shown) or more independent adsorption vessels containing beds. Regenerations are, advantageously, performed according to this invention in three steps.

At the end of each bed's adsorption cycle, the adsorption vessel which contains the loaded bed, for example vessel 60, is isolated from the process flow by means of valve 26 and valve 63. and depressured through manifold 62, valve 64, and manifold 51 to hydrocarbon recovery (not shown). Alternatively, vessel 40, is isolated from the process flow by means of valve 24 and valve 43. and depressured through manifold 42, valve 44, manifold 51 to hydrocarbon recovery.

During the first stage of regeneration dry inert gas, such as methane, ethane, or nitrogen which is, preferably, free of carbon oxides, unsaturated hydrocarbons and hydrogen is fed, from, for example a nitrogen gas supply system (not shown), through conduit 32, valve 52, and manifold 56 into exchanger 30 to control temperature during regeneration. Effluent from exchanger 30 flows through, manifold 31 and, alternately, through valve 38 and manifold 61 or valve 58 and manifold 41 into one of two adsorption vessels 40 and 60 thereby purging gaseous hydrocarbons therefrom to disposal through manifold 62, valve 64, manifold 51, valve 74, and conduit 75, or through manifold 42, valve 44, manifold 51, valve 74, and conduit 75 to disposal.

During the second stage of regeneration a reducing gas stream containing, predominantly, hydrogen is fed, from, for example a hydrogen gas supply system (not shown), through conduit 34, valve 54, and manifold 56 into exchanger 30 to control temperature during regeneration. Effluent from exchanger 30 flows through, manifold 31 and, alternately, through valve 38 and manifold 61 or valve 58 and manifold 41 into one of two adsorption vessels 40 and 60 to regenerate the adsorbent in the bed. Effluent from the vessel during regeneration flows therefrom to intermediate storage (not shown) through manifold 62, valve 68, and conduit 73 or through manifold 42, valve 44, manifold 51, valve 66 and conduit 73.

Where heating of the regeneration gas is desired, rates of temperature increase during the second stage of regeneration are, preferably, controlled to rates of less than about 11° C. per minute (about 20° F. per minute) while increasing temperature in the range of from about 4° C. to about 200° C. (about 40° F. to about 400° F.). Pressures of the hydrogen-rich reducing gas during the second stage of regeneration are, advantageously, in a range from about 5 psig to about 500 psig. While the reducing gas is flowing through the adsorbent bed, effluent gas composition is, periodically, monitored with gas analyzer 80. Second stage regeneration is complete when C2+ hydrocarbon levels in the effluent gas from the bed have been reduced to C2+ hydrocarbon levels in the feed.

Third stage regeneration involves purging all gaseous hydrogen from the adsorption vessel with an inert gas, e.g. nitrogen with or without a saturated hydrocarbon gas such as methane or ethane, while the vessel is at temperatures in a range upward from about 60° C. (140° F.). This involves blocking in valve 54 and opening valve 52 to switch from hydrogen to inert gas flow through the vessel. During this third stage of regeneration flow of inert gas, at or below ambient temperature and about 5 to about 100 psig, cools the vessel to about ambient temperature thereby completing the regeneration process.

Surface area of adsorbents can be determined by the Brunaur-Emmett-Teller (BET) method or estimated by a simpler Point B method. Adsorption data for nitrogen at the liquid nitrogen temperature, 77 K, are usually used in both methods. The Brunaur-Emmett-Teller equation, which is well known in the art, is used to calculate the amount of nitrogen for mono-layer coverage. The surface area is taken as the area for mono-layer coverage based on the nitrogen molecular area, 16.2 square Angstroms, obtained by assuming liquid density and hexagonal close packing. In the Point B method, the initial point of the straight portion of the Type II isotherm is taken as the completion point for the mono-layer. The corresponding amount adsorbed multiplied by molecular area yields the surface area.

Dispersion and surface area of active metal sites was determined by carbon monoxide chemisorption using a Pulse Chemisorb 2700 (Micromeritics). In this procedure, approximately 4 gram samples were purged with helium carrier gas, calcined in air at 500° C. for 1 hr, purged with helium, reduced in hydrogen at 500° C., purged with helium, and cooled to room temperature. The sample was treated with 49.5 percent carbon monoxide in helium and the dosed with 0.045 mL pulses of 49.5 percent carbon monoxide (CO), balance nitrogen, and the carbon monoxide uptake was measured by a thermal conductivity cell. Palladium dispersion values were calculated assuming one carbon monoxide molecule per palladium atom. Palladium loadings are weight percent palladium metal.

In characterizing the pore volume, both total pore volume and its distribution over the pore diameter are needed. The total pore volume is usually determined by helium and mercury densities or displacements. Helium, because of its small atomic size and negligible adsorption, gives the total voids, whereas mercury does not penetrate into the pores at ambient pressure and gives inter-particle voids. The total pore volume equals the difference between the two voids.

Palladium on a high-surface-area $\gamma$-$Al_2O_3$ is a preferred adsorbent for purification of olefins in accordance with this invention. In order to introduce palladium and/or other suitable metal ions on a high-surface-area $\gamma$-$Al_2O_3$, any known technique for monolayer dispersion can be employed. The phenomenon of spontaneous dispersion of metal oxides and salts in monolayer or submonolayer forms onto surfaces of inorganic supports with high surface areas has been studied extensively in the literature (e.g., Xie and Tang, 1990).

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Except were stated otherwise, ppm is parts per million by volume.

Comparative Example

This comparative example illustrates a process for purification of olefins effecting selective adsorption and/or complexing of the contained acetylenic impurities with the adsorbent in the presence of and essentially dihydrogen-free atmosphere within the bed of adsorbent. Comparison of this example with subsequent examples of the invention clearly show the advantageous results provided by admixing a source of dihydrogen with a gaseous olefinic mixture to form a feedstream comprising a sub-stoichiometric amount of dihydrogen based upon the total amount of acetylenic impurities present.

A 50 mL TEFLON-lined stainless steel pressure vessel was loaded with 37.54 gm of commercially available adsorbent (about 43 mL of 0.50 percent palladium on $\gamma$-$Al_2O_3$), and a centrally disposed thermocouple system to monitor bed temperatures. After this adsorption vessel was connected into a gas adsorption unit which provided required control of feed gases, temperatures, pressures, and analytical means, the adsorbent bed was run in the down-flow mode. Nitrogen was purged through the vessel before reducing the oxidized PdO/$\gamma$-$Al_2O_3$ adsorbent by heating to 49° C. in a flow of hydrogen. A circulating water bath was used to supply heat needed during reduction at 350 psig with hydrogen flowrates of about 70 mL/min. After 16 hours hydrogen flow was replaced with nitrogen flow. The vessel was maintained at a temperature of about 49° C. during the subsequent adsorption process.

After analysis of the effluent gases showed that hydrogen had been purged from the vessel, a feed mixture which contained 182 ppm acetylene in a balance of ethylene was introduced into the vessel and the vessel was pressurized to 250 psig. During adsorption the flow rate of the acetylene/ethylene mixture was 700 mL/min. and operating conditions of pressure and temperature were controlled to 200 psig and 49° C. By periodical analysis of effluent gas using an on-line gas chromatograph, acetylene was detected (less than about 0.5 ppm acetylene) breaking through the bed of adsorbent after a total of 122 L (1 atm and 21° C.) of feed gas was treated. In this example the adsorbent exhibited a capacity of about 0.51 mL of acetylene per mL of adsorbent.

After flow of the acetylene/ethylene mixture was stopped, the vessel was depressured to 1 atm and nitrogen was purged through the vessel for about 15 min. The vessel was maintained at 49° C. Adsorbent was regenerated using pure hydrogen at a flow rate of 70 mL/min. at 350 psig for about 18 hours.

Example 1

This example of the invention demonstrates the operation of an adsorption bed with 10 ppm of hydrogen added to the feed. The regenerated adsorbent bed from the Comparative Example was depressured to 1 atm and nitrogen was purged through the vessel for 15 minutes. After analysis of the effluent gases showed that hydrogen had been purged from the vessel, a feed mixture which contained 199 ppm acetylene and 10.3 ppm hydrogen in balance ethylene was introduced into the vessel and the vessel was pressurized to 200 psig. During adsorption the flow rate of the acetylene/hydrogen/ethylene mixture was 694 mL/min. and operating conditions of pressure and temperature were controlled at 200 psig and 490° C. By periodical analysis of effluent gas using an on-line gas chromatograph, acetylene was detected (less than about 0.5 ppm acetylene) breaking through the bed of adsorbent after a total of 127 L (1 atm and 21° C.) of feed gas was treated. In this example the adsorbent exhibited a capacity of about 0.58 mL of acetylene per mL of adsorbent.

After flow of the acetylene/hydrogen/ethylene mixture was stopped, the vessel was depressured to 1 atm and nitrogen was purged through the vessel for about 15 minutes. The vessel was maintained at 49° using the circulating water bath. The adsorbent was regenerated using pure hydrogen at a flow rate of 70 mL/min. at 350 psig for about 18 hours.

Example 2

This example of the invention demonstrates the operation of an adsorption bed with 44 ppm of hydrogen added to the feed. The regenerated adsorbent bed from the Comparative Example was depressured to 1 atm and nitrogen was purged through the vessel for 15 minutes. After analysis of the effluent gases showed that hydrogen had been purged from the vessel, a feed mixture which contained 198 ppm acetylene and 44.1 ppm hydrogen in balance ethylene was introduced into the vessel and the vessel was pressurized to 200 psig. During adsorption the flow rate of the acetylene/hydrogen/ethylene mixture was 672 mL/min. and operating conditions of pressure and temperature were controlled at 200 psig and 49° C. By periodical analysis of effluent gas using an on-line gas chromatograph, acetylene was detected (less than about 0.5 ppm acetylene) breaking through the bed of adsorbent after a total of 205 L (1 atm and 21° C.) of feed gas was treated. In this example the adsorbent exhibited a capacity of about 0.93 mL of acetylene per mL of adsorbent.

After flow of the acetylene/hydrogen/ethylene mixture was stopped, the vessel was depressured to 1 atm and nitrogen was purged through the vessel for about 15 minutes. The vessel was maintained at 49° C. using the circulating water bath. The adsorbent was regenerated using pure hydrogen at a flow rate of 70 mL/min. at 350 psig for about 18 hours.

Example 3

This example of the invention demonstrates the operation of an adsorption bed with 113 ppm of hydrogen added to the feed. The regenerated adsorbent bed from the Comparative Example was depressured to 1 atm and nitrogen was purged through the vessel for 15 minutes. After analysis of the effluent gases showed that hydrogen had been purged from the vessel, a feed mixture which contained 198 ppm acetylene and 113 ppm hydrogen in balance ethylene was introduced into the vessel and the vessel was pressurized to 200 psig. During adsorption the flow rate of the acetylene/hydrogen/ethylene mixture was 682 mL/min. and operating conditions of pressure and temperature were controlled at 200 psig and 49° C. An attempt was made to detect acetylene breakthrough by periodical analysis of effluent gas using an on-line gas chromatograph. After eight hours on-stream breakthrough was still not detected and the experiment had to be discontinued. By this time a total of 336 L (1 atm and 21° C.) of feed gas had been treated by the bed. In this example the adsorbent exhibited a capacity of at least 1.51 mL of acetylene per mL of adsorbent.

After flow of the acetylene/hydrogen/ethylene mixture was stopped, the vessel was depressured to 1 atm and nitrogen was purged through the vessel for about 15 minutes. The vessel was maintained at 49° C. using the circulating water bath. The adsorbent was regenerated using pure hydrogen at a flow rate of 70 mL/min. at 350 psig for about 18 hours.

Examples 1–3 above clearly show the benefits of adding sub-stoichiometric amounts of hydrogen on adsorbent capacity. Those skilled in the art will recognize that adding hydrogen to the adsorber feed may lead to simple hydrogenation reactions such as acetylene hydrogenation to ethylene:

$$C_2H_2 + H_2 => C_2H_4.$$

Because acetylene is adsorbed in this system and ethylene is not, such a reaction would result in an increase in acetylene breakthrough time, and therefore an apparent increase in acetylene adsorption capacity as measured in the experiments.

The magnitude of the impact of added hydrogen on this mechanism can be easily determined from the stoichiometry of the above acetylene hydrogenation reaction. It is clear that for every mole of hydrogen added, one mole of acetylene can be hydrogenated. The impact of hydrogenation reactions on apparent adsorption capacity can therefore be easily calculated. The results are shown in Table I and FIG. 2 for various levels of hydrogen addition from the examples, and compared with laboratory measured acetylene adsorption capacities.

TABLE I

COMPARISON OF OBSERVED ADSORPTION CAPACITY AND APPARENT CAPACITY FROM SIMPLE HYDROGENATION

| Molar Ratio of Dihydrogen to Acetylene | Observed Adsorption Capacity | Apparent Adsorption Capacity |
| --- | --- | --- |
| 0.0 | 0.51 | 0.51 |
| 0.05 | 0.58 | 0.54 |
| 0.22 | 0.93 | 0.65 |
| 0.57 | >1.51 | 1.18 |

Adsorption capacity in mL of acetylene per mL of adsorbent.

Figure 2:
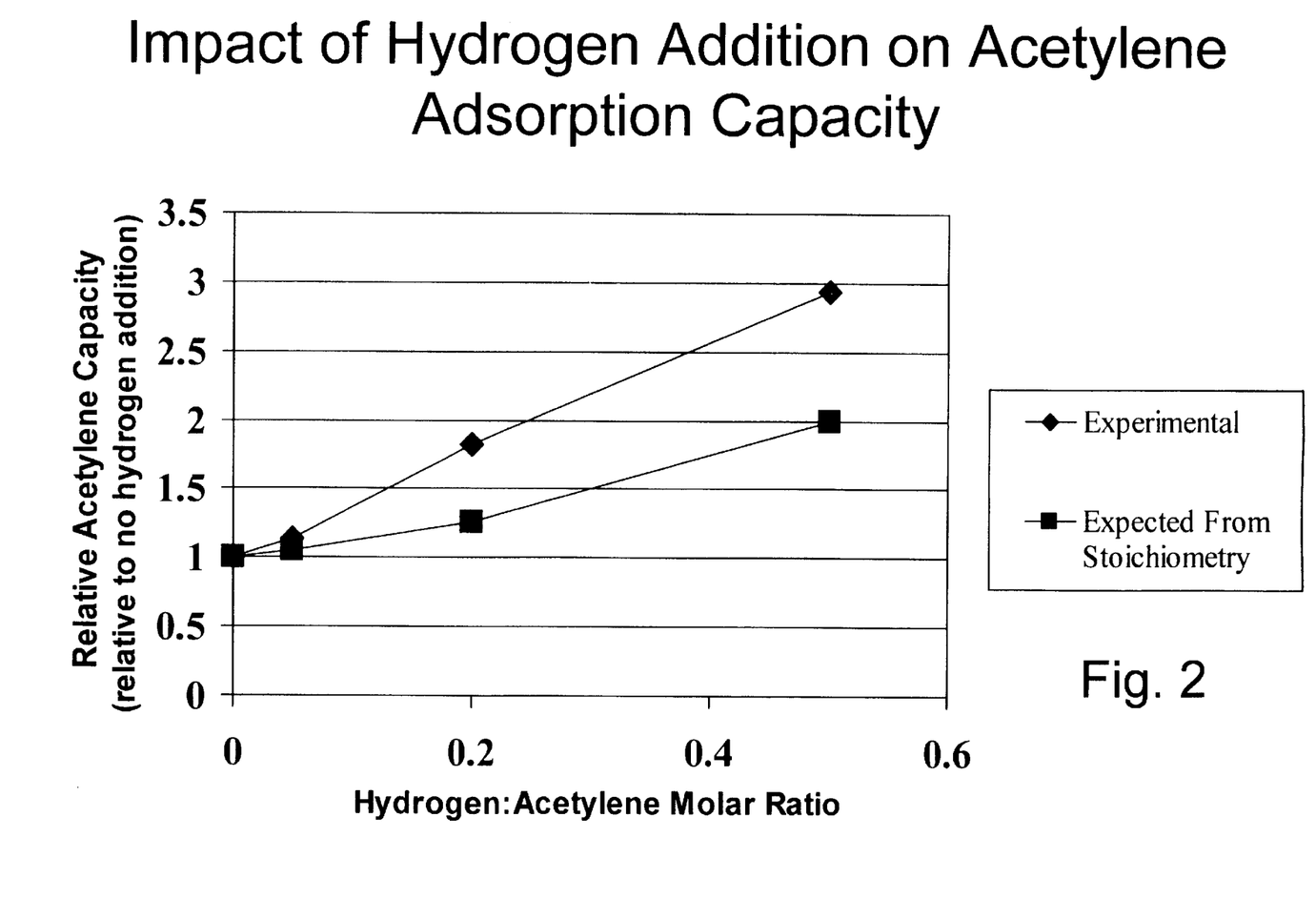
FIG. 2 is a graphical illustration of the unexpected impact of sub-stoichiometric levels of dihydrogen on acetylene adsorption capacity in processes for purification of olefins according to the invention.

It clear from the data shown in Table I and FIG. 2 that the adsorption capacity increase from sub-stoichiometric dihydrogen addition is significantly larger than can be explained by simple hydrogenation reaction. This critical result is unexpected and unpredictable based upon know acetylene hydrogenation stoichiometry.

Examples have been presented and hypotheses advanced herein in order to better communicate certain facets of the invention. The scope of the invention is determined solely by the scope of the appended claims.

For the purposes of the present invention, "predominantly" is defined as more than about ninety per cent. "Substantially" is defined as occurring with sufficient frequency or being present in such proportions as to measurably affect macroscopic properties of an associated compound or system. Where the frequency or proportion for such impact is not clear substantially is to be regarded as about twenty per cent or more. The term "Essentially" is defined as absolutely except that small variations which have no more than a negligible effect on macroscopic qualities and final outcome are permitted, typically up to about one percent.

That which is claimed is:

1. A process for purification of olefins which comprises: providing a impure mixture comprising at least one olefin of from 2 to about 8 carbon atoms, acetylenic impurities having the same or similar carbon content in an amount of up to about 1 percent by volume based upon conversion of the total amount of olefin present and optionally saturated hydrocarbon gases;

admixing a source of dihydrogen with the impure mixture to form a feedstream comprising a sub-stoichiometric amount of dihydrogen based upon the total amount of acetylenic impurities present to their olefiric analogs:

passing the feedstream through a particulate bed of adsorbent comprising predominantly a support material selected from the group consisting of alumina, silica, active carbon and clay, containing less than 500 parts per million by weight of sulfur-containing components, calculated as elemental sulfur, and having a high surface area from about 80 to about 500 square meters per gram as measured by the BET gas adsorption method, on which is dispersed at least one metallic element in the zero valent—state selected from the group consisting of chromium, iron, cobalt, nickel, copper, ruthenium, palladium, silver and platinum, to effect, under conditions suitable for adsorption within, the bed, selective adsorption and/or complexing of the contained acetylenic contaminants with the adsorbent, until levels of the acetylenic impurities in the purified effluent increase to a predetermined level of less than about 1 part per million by volume of the acetylenic impurities; and thereafter regenerating the resulting bed of adsorbent in the presence of a reducing gas comprising dihydrogen to effect release of the contained acetylenic impurities from the adsorbent.

2. The process according to claim 1 wherein the adsorbent further comprises at least one element selected from the group consisting of lithium, sodium, potassium, zinc, molybdenum, tin, tungsten, and iridium, dispersed on the support material.

3. The process according to claim 1 wherein the metal dispersed on the support material is at least one element selected from the group consisting of iron, cobalt, nickel, copper, palladium, silver and platinum, and the absorbent has a dispersed metal content in a range of from about 0.01 to about 10 percent based on the total weight of the adsorbent.

4. The process according to claim 3 wherein the feedstream passes though the bed of particulate adsorbent at gas hourly space velocities in a range of from about 0.05 hours-, to about 20,000 hours-, measured at standard conditions of 0° C. and 760 mm Hg.

5. The process according to claim 1 wherein the adsorbent comprises at least about 90 weight percent of a gamma alumina having surface area in a range of from about 80 to about 500 square meters per gram as measured by the BET gas adsorption method.

6. The process according to claim 5 wherein the metal dispersed on the support material is palladium, and the absorbent has a palladium content in a range of from about 0.01 to about 10 percent based on the total weight of the adsorbent.

7. The process according to claim 1 wherein the olefin in the impure mixture being purified is predominantly ethylene or propylene, the impure mixture contains less than about 1 parts per million by volume of mercury-containing, arsenic-containing, and sulfur-containing components, each calculated as the element, and wherein the feedstream, while passing through the bed, is at temperatures in a range of from about 55° C. to about 65° C.

8. The process according to claim 7 wherein the adsorbent comprises at least about 90 weight percent of a gamma alumina having surface area in a range of from about 150 to about 350 square meters per gram as measured by the BET gas adsorption method, and wherein the metal dispersed on the support material is palladium, and the absorbent has a palladium.

9. The process according to claim 1 wherein the adsorbent contains less than 500 parts per million by weight of a sulfur-containing component, calculated as elemental sulfur.

10. A process for purification of olefins produced by thermal cracking of hydrocarbons which comprises:

providing a impure mixture comprising at least about 99 percent by volume of an olefin having from 2 to about 4 carbon atoms, and acetylenic impurities having the same or similar carbon content in an amount in a range upward from about 1 to about 1000 parts per million by volume;

admixing a source of dihydrogen with the impure mixture to form a feedstream comprising a sub-stoichiometric amount of dihydrogen based upon the total amount of acetylenic impurities present;

passing the feedstream through a particulate bed of adsorbent comprising predominantly a support material selected from the group alumina, silica, active carbon, and clay, containing less than 500 parts per million by weight of sulfur-containing components, calculated as elemental sulfur, and having a surface area in a range of from about 80 to about 500 square meters per gram as measured by the BET gas adsorption method, on which is dispersed at least one metallic element selected from the group consisting of chromium, iron, cobalt, nickel, copper, ruthenium, palladium, silver and platinum, to provide an effluent stream from the bed;

effecting, under conditions suitable for adsorption within the bed, selective adsorption and/or complexing of the contained acetylenic contaminants with the adsorbent, until levels of the acetylenic impurities in the effluent stream increase to a predetermined level in a range downward from about 1 parts per million by volume; and thereafter regenerating the resulting bed of adsorbent in the presence of a reducing gas comprising dihydrogen to effect release of the contained acetylenic impurities from the adsorbent.

contains less than about 1 part per million by volume of the acetylenic impurities; and thereafter regenerating the resulting bed of adsorbent in the presence of a reducing gas comprising dihydrogen to effect release of the contained acetylenic impurities from the adsorbent.

11. The process according to claim 10 wherein the adsorbent further comprises at least one element selected from the group consisting of lithium, sodium, potassium, zinc, molybdenum, tin, tungsten, and iridium, dispersed on the support material.

12. The process according to claim 10 wherein the metal dispersed on the support material is at least one element selected from the group consisting of iron, cobalt, nickel, copper, ruthenium, palladium, silver and platinum, and the absorbent has a dispersed metal content in a range of from about 0.01 to about 10 percent based on the total weight of the adsorbent.

13. The process according to claim 12 wherein the feedstream passes though the bed of particulate adsorbent at space velocities in a range of from about 0.05 hours-1 to about 20,000 hours-1 measured at standard conditions of 0° C. and 760 mm Hg.

14. The process according to claim 10 wherein the adsorbent comprises at least about 90 weight percent of a gamma alumina having surface area in a range of from about 80 to about 500 square meters per gram as measured by the BET gas adsorption method, and contains less than 500 parts per million by weight of a sulfur-containing component, calculated as elemental sulfur.

15. The process according to claim 14 wherein the metal dispersed on the support material is palladium, and the absorbent has a palladium content in a range of from about 0.01 to about 10 percent based on the total weight of the adsorbent.

16. A process according to claim 10 wherein the olefin in the impure mixture being purified is predominantly ethylene or propylene, the impure mixture contains less than about 1 parts per million by volume of mercury-containing, arsenic-containing, and sulfur-containing components, each calculated as the element, and wherein the impure mixture, while passing through the bed, is at temperatures in a range of from about 5° C. to about 65° C.

17. The process according to claim 16 wherein the adsorbent comprises at least about 90 weight percent of a gamma alumina having surface area in a range of from about 150 to about 350 square meters per gram as measured by the BET gas adsorption method, and wherein the metal dispersed on the support material is palladium, and the absorbent has a palladium content in a range of from about 0.01 to about 10 percent based on the total weight of the adsorbent.

* * * * *

UNITED STATES PATENT AND TRADEMARK OFFICE
CERTIFICATE OF CORRECTION

PATENT NO.    : 6,680,419 B2
DATED         : January 20, 2004
INVENTOR(S)   : Larry C. Satek, Michael J. Fornal and Diadema N. Ventura It is certified that error appears in the above-identified patent and that said Letters Patent is hereby corrected as shown below:

<u>Column 17,</u>
Lines 22-23, should read -- in a range of from about 5ºC to about 65ºC. -- instead of "in a range of from about 55ºC to about 65ºC"

Signed and Sealed this

Twenty-third Day of March, 2004

JON W. DUDAS
*Acting Director of the United States Patent and Trademark Office*